United States Patent [19]
Mittelman

[11] Patent Number: 5,413,600
[45] Date of Patent: May 9, 1995

[54] NASAL-LABIAL IMPLANT

[76] Inventor: Harry Mittelman, 23 Heather Dr., Atherton, Calif. 94027

[21] Appl. No.: 64,836

[22] Filed: May 19, 1993

[51] Int. Cl.$^6$ ............................................. A61F 2/02
[52] U.S. Cl. .................................... 623/11; 623/10
[58] Field of Search ............... 623/10, 11, 16, 66, 623/12, 18, 1

[56] References Cited

U.S. PATENT DOCUMENTS 4,969,901 11/1990 Binder ................................. 623/11
4,990,160 2/1991 Terino ................................. 623/11

FOREIGN PATENT DOCUMENTS 0357927 3/1990 European Pat. Off. ............. 623/16
0518278 12/1992 European Pat. Off. ............. 623/16
2447182 9/1980 France ................................. 623/11

Primary Examiner—David Isabella
Assistant Examiner—Debra S. Brittingham

[57] ABSTRACT

An implant is disclosed for disguising the effects of aging and/or trauma in the nasal-labial area of the face.

9 Claims, 3 Drawing Sheets

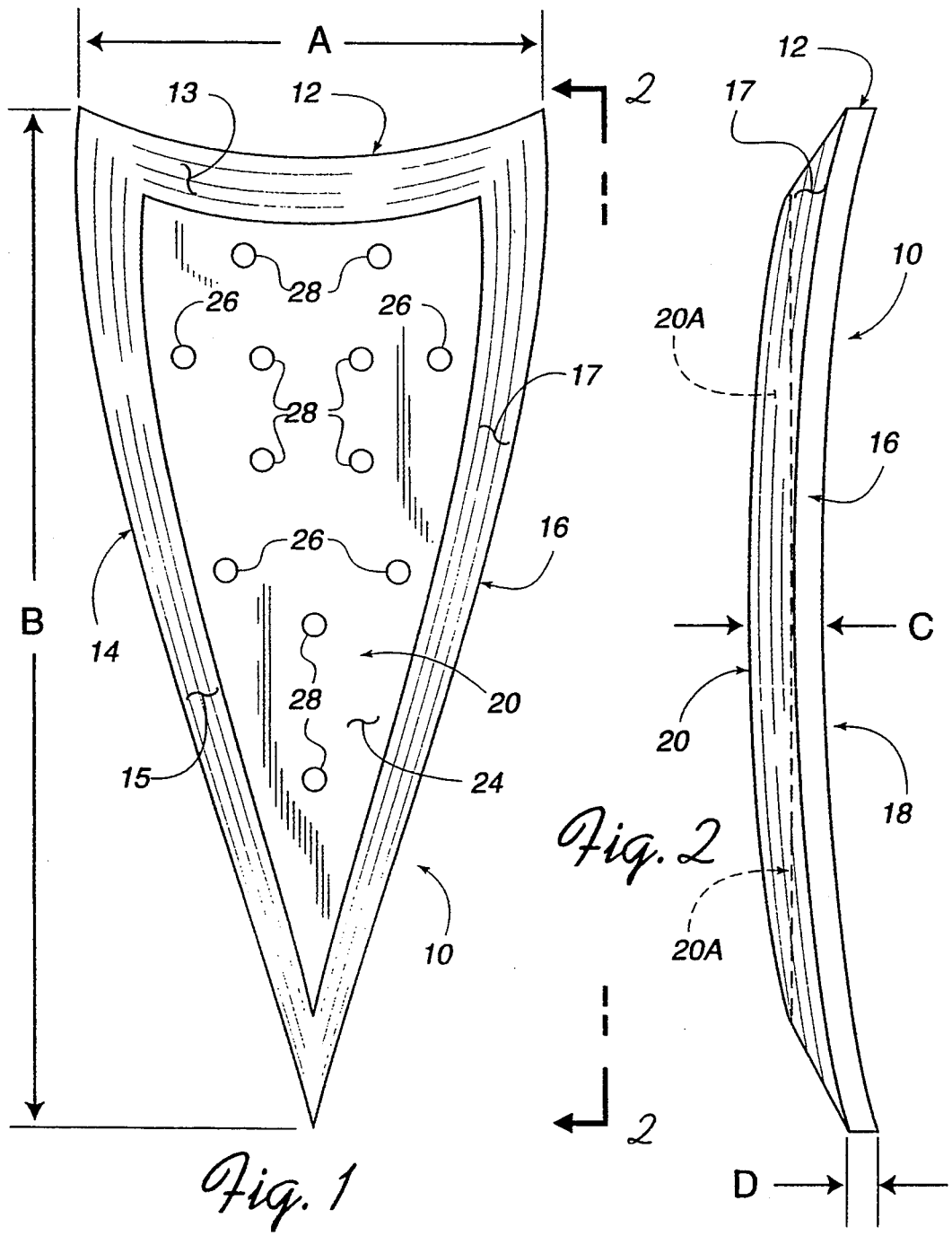

NASAL-LABIAL IMPLANT

TECHNICAL FIELD OF THE INVENTION

The present invention relates generally to implants for facial plastic surgery. It relates in particular to an implant for disguising effects of aging in a facial area generally referred to as the nasal-labial groove.

DISCUSSION OF BACKGROUND ART

One effect of aging in human beings is a deepening of an area of the face between the nose and the lateral corners of the mouth. This area is referred to by practitioners of facial plastic surgery as the nasal-labial groove. It is also referred to as the melo-labial groove or the labial-facial groove.

As aging proceeds, this area becomes deeper and deeper due to loss of subcutaneous fat pads in the area. In addition, soft tissues of the cheeks may begin to change position and fall inferiorly, and skin may become looser, both of which processes accentuate the deepening of the nasal-labial groove. Such a groove may also be the result of or accentuated by facial trauma or infection.

Conventional facelift surgery may provide considerable improvement of an aging face in certain areas. Such surgery is particularly effective in the lower third of the face and the upper half of the neck. Generally, however, deepening of the nasal-labial groove is not improved dramatically by conventional facelift surgery. Attempts to improve the appearance of the nasal-labial groove frequently result in a facial appearance which is unnatural and may be described as a "pulled back" or a "wind-blown" appearance.

Many patients in their late thirties or early forties become concerned about the deepening of the nasal-labial groove but are less concerned about other aging processes in their face and are thus reluctant, at this age, to undertake something as drastic as facelift surgery. For such patients, an implant method of raising and softening the nasal-labial groove would generally be preferable to conventional facelift surgery.

An implant intended for improving the appearance of the submalar area is described in U.S. Pat. No. 4,969,901, the disclosure of which is hereby incorporated by reference. The implant is insertable intraorally by accepted methods known to those familiar with facial plastic surgery procedures. The implant has an elongated tear drop shape and a generally arch-like cross section. The cross section is, for the most part of the implant, a high arch-like cross section with steeply falling sides.

It is believed that an implant of the type described in U.S. Pat. No. 4,969,901, while effective in plumping the submalar area, is not effective or predictable in softening a developing nasal-labial groove. Its position is lateral to the nasal-labial groove and its main purpose is augmenting the submalar space. This implant is designed to be placed in a subperiosteal and submalar implant position.

There is a need for a nasal-labial implant which is easily insertable by known non-invasive methods, but which is designed to be essentially undetectable as an implant after insertion, and whose unique and primary purpose and function is to augment and reduce the prominence of the nasal-labial groove.

SUMMARY OF THE INVENTION

It is an object of this invention to provide a nasal-labial implant which is subcutaneously or subperiostially insertable in a patient's face by established methods and which is essentially undetectable as an implant, visually or palpably, after insertion. It is a further object of the invention to provide an implant which may be made from a wide variety of synthetic materials.

The above and other objects of the present invention are achieved by providing an implant comprising a generally triangular sheet of a body-compatible material. The implant has upper and lower surfaces and first second and third sides defining respectively first second and third edges. The first side has a concave curvature and forms a base of the implant for location at the junction of the lateral nasal alar groove with the nasal-labial groove. The second and third sides of the implant are each longer than the first side and have a convex curvature. A junction of the second and third sides forms a tail of the implant. The first second and third edges of the sheet are bevelled or feathered such that the implant is substantially undetectable as such, visually or palpably, after insertion.

The implant is preferably formed from a material selected from a group consisting of silicone-containing elastomers, fabric including fluorinated-hydrocarbon-polymer, animal and human-like collagen, collagen compounds, vicryl mesh, polyimid mesh, and hyaluronic acid compounds.

Preferably, the deep or posterior surface of the implant is generally concave and adjusted to the facial curvature of a particular patient's face in the nasal-labial region. The outer or anterior surface may be flat or convex shape, the shape depending on a desired cosmetic effect.

The base of the implant may have a length preferably between about 0.2 and 2.0 centimeters (cm), and a height preferably of between about 1.0 cm and 5.0 cm, the height being defined as the distance between the base and the tail of the implant.

The implant may have a maximum thickness preferably between about 0.1 cm and 0.9 cm and the bevelled edges of the sheet may have a minimum thickness preferably between about 0.1 cm and 0.8 cm.

Preferably, the implant includes a plurality of perforations or fenestrations extending therethrough. A suture may be passed through a perforation for suturing the implant in position on a patient's face. Additional or alternative perforations may be provided, for allowing scar tissue to grow through the implant after it is inserted, thus providing means for stabilizing the implant after insertion, and for preventing it from moving, superiorly or inferiorly, in the event of trauma or applied pressure.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

FIG. 1 is a plan view schematically illustrating one embodiment a nasal-labial implant in accordance with the present invention.

FIG. 2 is an elevation view seen generally in the direction 2—2 of FIG. 1 schematically illustrating the implant of FIG. 1.

DESCRIPTION OF PREFERRED EMBODIMENT(S) OF THE INVENTION

Figure 3A:
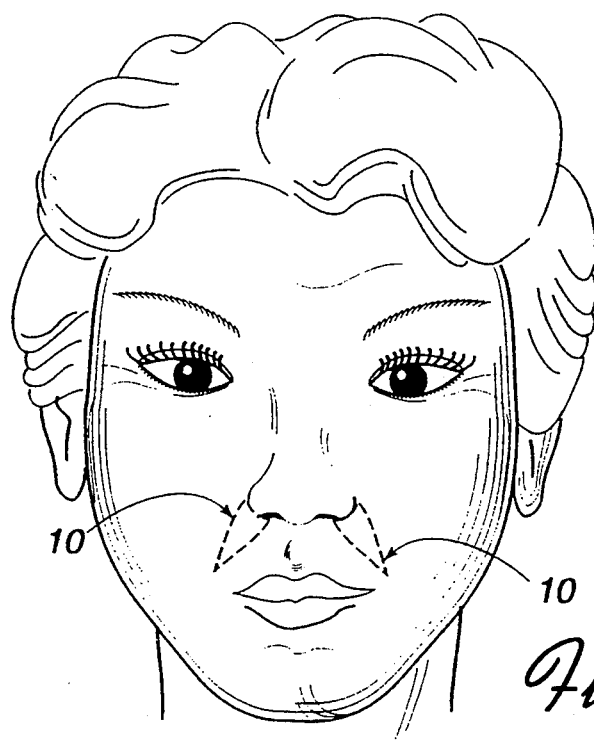
FIGS. 3A and B are pictorial views illustrating one preferred subdural placement of the implant of FIG. 1 along the nasal-labial groove.

Turning now to the drawings, one embodiment of an implant 10 in accordance with the present invention is illustrated in FIGS. 1 and 2. The implant has a triangular or shield-like form and preferably is formed from a sheet of a body-compatible material. Preferred materials for the implant 10 include silicone-containing elastomers, fabric including fluorinated-hydrocarbon-polymer, animal and human-like collagen, collagen compounds, vicryl mesh, polyimid mesh and hyaluronic acid compounds.

One side 12 of implant 10 has a concave curvature and forms what may be referred to as the base of the implant. Sides 14 and 16 each have a convex curvature. A junction 19 of sides 14 and 16 may be referred to as the tail of the implant.

The implant has a concave posterior or deep surface 18 (see FIG. 2). This posterior or deep surface is the surface of implant 10 which would normally rest in contact with a patient's facial soft tissue fat or muscle or skeleton, and subcutaneously under the nasal labial groove structure. The concave curvature may be selected by a surgeon to best match facial contours of a particular patient.

An outer or anterior surface 20 of implant 10 is the surface which imparts a desired contour after the implant is placed. Surface 20 usually has a generally convex curvature, but may also be generally flat, as indicated by broken line 20A. This surface can be adjacent to the deep surface of the skin, but may be placed even deeper.

It is particularly important in implant surgery that an implant not be detectable as such after it is in position. It should certainly not be visibly detectable as an implant, and should, preferably, also not be palpably detectable as an implant. Accordingly, along sides 12, 14, and 16 of implant 10 the thickness of the implant is, preferably, reduced in a tapered fashion to provide bevelled or feathered edges 13, 15, and 17 on the implant.

Figure 3B:
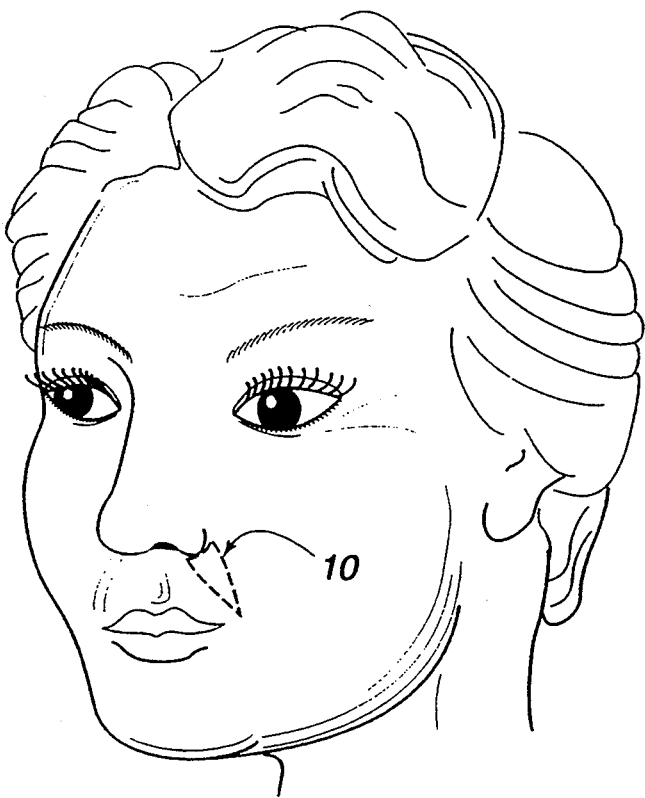

FIGS. 3A and 3B illustrate an exemplary subcutaneous positioning of implant 10 relative to the nasal-labial groove. The implant is located with base 12 parallel to the lateral nasal alar groove and with tail 19 oriented toward the inferior portion of the nasal-labial groove.

It is intended that the implant of the present invention be made in a range of sizes, each size having the same general shape, to accommodate varying needs of different patients. Base 12 preferably has a length A between about 0.2 cm and 2.0 cm, and a height B, i.e., a distance between base 12 and tail 19, of between about 1.0 cm and 5.0 cm.

As discussed above, anterior and posterior surfaces 18 and 20 may each have a curvature. Because of this, even in region 24, FIG. 1, between bevelled edges 13, 15, and 17, the thickness of the implant is not necessarily constant. For descriptive purposes, however, a maximum thickness C (see FIG. 2) may be specified. This maximum thickness C may be found anywhere within region 24. The maximum thickness C is preferably between about 0.1 cm and 0.9 cm. Bevelled edges 13, 15, and 17 of the implant preferably have a minimum thickness D between about 0.1 cm and 0.8 cm.

Referring again to FIG. 1, in one aspect of the present invention a plurality of suture holes 26 or fenestration holes 28 are provided in the implant. These holes extend completely through the implant. Fenestration holes 28 allow the growth of scar tissue through implant 10 after it is subcutaneously implanted. This helps stabilize the implant and keeps it from moving superiorly or inferiorly due to trauma or applied pressure. The suture holes 26, preferably located proximate the edges of implant 10, preferably are each configured to allow passage of suture or a suture needle. This facilitates temporary suturing of a subcutaneously placed implant to a patients external skin. Such temporary suturing may be used to hold an implant in position for two or three days, or even a week or two, following surgery. Once scar tissue has grown, temporary suturing may be removed and the implant will be held in position by scar tissue.

Figure 4:
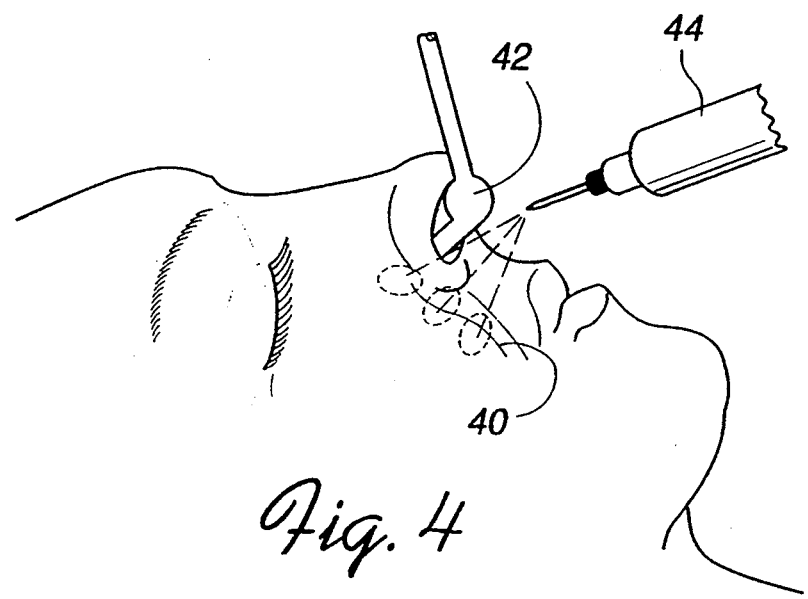
FIG. 4 depicts injection of a local anesthetic along the nasal-labial groove preparatory to making an incision and placement of the nasal-labial implant.
Figure 5:
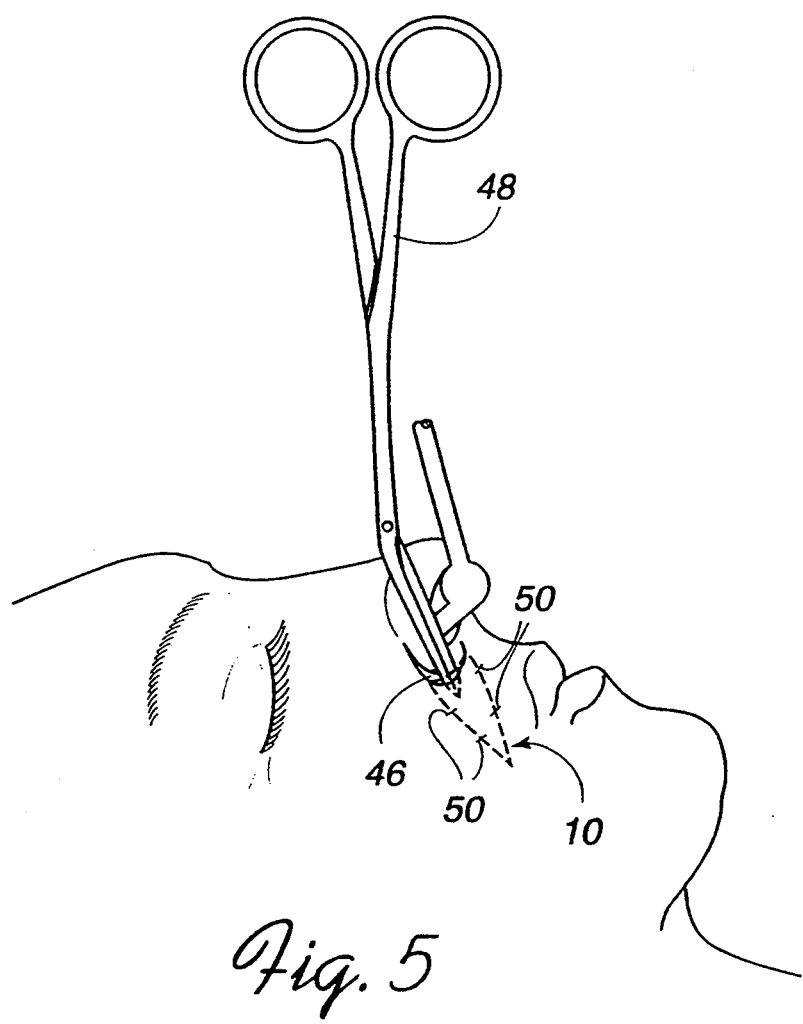
FIG. 5 illustrates an exemplary incision and placement of the nasal-labial implant.

FIGS. 4 and 5 are illustrate schematically a suitable process for preparing a patient for, and placement of a nasal-labial implant 10 along a nasal-labial groove 40 in accordance with my invention. Initially, an instrument such as a nasal speculum 42 is used to expose the nasal vestibule, and a syringe 44 is used to inject a local anesthetic along the nasal-labial groove 40. Then, referring to FIG. 5, a transnasal lateral vestibular incision 46 is made along the nasal labial groove with subdermal subcutaneous undermining, for placement of the implant 10. A grasping forceps instrument 48 is used to position the implant 10 as described previously, for example, in FIGS. 3A and 3B, then, optionally, sutures 50 may be applied via holes 26, and the incision 46 is closed.

The present invention has been described in terms of a preferred embodiment and a number of other embodiments. The invention however is not limited to the embodiments described and depicted. Rather, the scope of the invention is defined by the appended claims.

What is claimed is:

1. An implant for the nasal labial groove of the face, comprising:

a generally triangular elongated arrowhead-shaped sheet of a body-compatible material, the sheet having a first side and elongated second and third sides defining a peripheral edge comprising respectively first, second and third edges, and the implant having anterior and posterior surfaces;

the first side having a concave curvature and forming a base of the implant for location in the nasal labial groove;

the elongated second and third sides having a convex curvature and being symmetrical one to the another, a junction of the second and third sides forming a tail of the implant; and the peripheral edge of the sheet being bevelled.

2. The implant of claim 1 wherein the body-compatible material is selected from a group consisting of silicone-containing elastomers, fabric including fluorinated-hydrocarbon polymer, synthetic, animal and homologous human collagen, collagen compounds, vicryl mesh, polyimid mesh and hyaluronic acid compounds.

3. The implant of claim 1 wherein the posterior or deep surface is concave and the anterior or outer surface is convex.

4. The implant of claim 1 wherein the posterior or deep surface is generally concave and the anterior or outer surface is flat.

5. The implant of claim 1 wherein the base has a length between about 0.2 and 2.0 centimeters, and a height of between about 1.0 and 5.0 centimeters, the height defined as a distance between the base and the tail.

6. The implant of claim 5 wherein the sheet has a maximum thickness between about 0.1 and 0.9 centimeters and the bevelled edges of the sheet have a minimum thickness between about 0.1 and 0.8 centimeters.

7. The implant of claim 1 wherein the sheet includes a plurality of apertures extending therethrough, for facilitating suturing the implant in a subcutaneous position along a patient's nasal-labial groove.

8. The implant of claim 1 wherein the sheet includes a plurality of apertures extending therethrough, for permitting the growth of scar tissue through the implant when the implant is subcutaneously implanted along a patient's nasal-labial groove.

9. The implant of claim 1 where the sheet includes a plurality of apertures extending therethrough for at least one of facilitating suturing the implant in a subcutaneous position along a patient's nasal-labial groove and permitting the growth of scar tissue through the implant when the implant is subcutaneously implanted along a patient's nasal-labial groove.

* * * * *